US011077153B2

(12) United States Patent
Mogna

(10) Patent No.: US 11,077,153 B2
(45) Date of Patent: *Aug. 3, 2021

(54) **COMPOSITION FOR USE IN TREATING OR PREVENTING VIRAL OR BACTERIAL INFECTIONS IN A SUBJECT UNDERGOING ANTI-TUMOR CHEMOTHERAPY, LEUKEMIA TREATMENT OR AIDS THERAPY COMPRISING *L. REUTERI* LER03 AND/OR *L. SALIVARIUS* LS06**

(71) Applicants: Chiara Benassai, Novara (IT); Elena Mogna, Novara (IT); Vera Mogna, Novara (IT)

(72) Inventor: Giovanni Mogna, Novara (IT)

(73) Assignee: Chiara Benassai et al., Novara (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/307,757

(22) PCT Filed: Apr. 30, 2015

(86) PCT No.: PCT/IB2015/000614
§ 371 (c)(1),
(2) Date: Oct. 28, 2016

(87) PCT Pub. No.: WO2015/170159
PCT Pub. Date: Nov. 12, 2015

(65) Prior Publication Data
US 2017/0112883 A1    Apr. 27, 2017

Related U.S. Application Data

(63) Continuation of application No. PCT/IB2015/000614, filed on Apr. 30, 2015.

(30) Foreign Application Priority Data

May 5, 2014 (IT) .............................. MI2014A0815

(51) Int. Cl.
| A61K 35/744 | (2015.01) |
| A61K 35/74 | (2015.01) |
| A61K 9/06 | (2006.01) |
| A61K 35/745 | (2015.01) |
| A61K 35/747 | (2015.01) |

(52) U.S. Cl.
CPC .............. *A61K 35/744* (2013.01); *A61K 9/06* (2013.01); *A61K 35/74* (2013.01); *A61K 35/745* (2013.01); *A61K 35/747* (2013.01)

(58) Field of Classification Search
CPC ........ A61K 35/744; A61K 35/74; A61K 9/06; A61K 35/745; A61K 35/747; A61K 31/715; A61K 31/734; A61K 36/886; A61P 31/18; A61P 31/12; A61P 31/04
See application file for complete search history.

(56) References Cited

U.S. PATENT DOCUMENTS

| 6,103,227 A | 8/2000 | Wolf et al. |
| 2009/0274672 A1 | 11/2009 | Yu et al. |
| 2010/0143305 A1 | 6/2010 | Lemke |
| 2010/0203018 A1 | 8/2010 | Benedetti et al. |
| 2011/0117210 A1 | 5/2011 | Ugolkov |
| 2012/0107395 A1 | 5/2012 | Xie et al. |
| 2013/0309212 A1 | 11/2013 | Zhang et al. |
| 2017/0042951 A1 | 2/2017 | Mogna |

FOREIGN PATENT DOCUMENTS

| CN | 1370587 A | 9/2002 |
| EP | 1567018 B1 | 7/2009 |
| EP | 2173195 B1 | 9/2015 |
| JP | 2008237687 A | 10/2003 |
| JP | 2007084533 A | 4/2007 |
| JP | 2009269906 A | 11/2009 |
| JP | 2010534470 A | 11/2010 |
| JP | 2012180289 A | 9/2012 |
| KR | 20100049827 A | 5/2010 |
| KR | 20130048946 A | 5/2013 |

(Continued)

OTHER PUBLICATIONS

International Search Report and Written Opinion for International Patent Application No. PCT/IB2015/000614 filed Apr. 30, 2015 on behalf of Giovanni Mogna. dated Jul. 8, 2015. 11 pages.
WPI/Thomson Scientific; Database "XP002728393 & KR20100049827A" May 13, 2010. 2 pages.
WPI/Thomson Scientific; Database "XP002728394 & KR20130048946A" May 13, 2013. 2 pages.
Notice of Allowance for U.S. Appl. No. 15/307,756, filed Oct. 26, 2018 on behalf of Gioanni Mogna. dated Apr. 24, 2019 (8 pages).
Habriev R.U., pp. 523-541 2005 (13 pages) (Original + Abstract Only).
International Search Report for Russian Application No. 2016143921/ 04 (070429) filed Apr. 30, 2015. dated Dec. 17, 2018 (11 pages) (Original + English Translation) 4 pages.

(Continued)

*Primary Examiner* — Kade Ariani
(74) *Attorney, Agent, or Firm* — Steinfl + Bruno, LLP

(57) ABSTRACT

A composition for use as adjunctive therapy to antitumor chemotherapeutic treatments, acquired immunodeficiency syndrome treatments and leukemia treatments is described. The composition includes a strain of bacteria *Lactobacillus reuteri* LRE 03 DSM 23879 which is able to strongly stimulate the production of pro-inflammatory cytokines (Th1) interferon INF-gamma, the cytokines exhibiting a marked antiviral and/or antibacterial activity, and/or a bacterial strain *Lactobacillus salivarius* LS06 DSM 26037 which is able to strongly stimulate dendritic cell production, the dendritic cells exhibiting a marked antiviral and/or antibacterial activity. The composition can include one or more of: a bacterial strain able to produce, when ingested, bacterial exopolysaccharides EPS; and/or a plant polysaccharide such as tara gum; and/or an *Aloe arborescens* gel; and/or a gelling agent such as sodium alginate and/or a highly bioavailable zinc internalized into a tyndallized bacterial cell.

20 Claims, 6 Drawing Sheets

(56) References Cited

FOREIGN PATENT DOCUMENTS

| WO | 2007/015132 A2 | 2/2007 |
|---|---|---|
| WO | 2009/013709 A2 | 1/2009 |
| WO | 2012/143787 A1 | 10/2012 |
| WO | 2013/034974 A1 | 3/2013 |
| WO | 2013/084052 A1 | 6/2013 |
| WO | 2013/114185 A1 | 8/2013 |
| WO | 2014/020408 A1 | 2/2014 |
| WO | 2015/170158 A1 | 11/2015 |
| WO | 2015/170159 A1 | 11/2015 |

OTHER PUBLICATIONS

Office Action for Russian Application No. 2016143921/04 (070429) filed Apr. 30, 2015. dated Dec. 17. 2018 (11 pages) (Original + English Translation) 11 pages.
International Preliminary Report on Patentability for International Application No. PCT/IB2015/000614 filed on Apr. 30, 2015 on behalf of Giovanni Mogna dated Nov. 8, 2016 7 pages.
International Search Report for International Application No. PCT/IB2015/000602 filed on Apr. 30, 2015 on behalf of Giovanni Mogna. dated Aug. 3, 2015. 4 pages.
Non-Final Office Action for U.S. Appl. No. 15/307,756, filed Oct. 28, 2016, on behalf of Giovanni Mogna. dated Oct. 4, 2018. 10 pgs.
Restriction Requirement for U.S. Appl. No. 15/307,756, filed Oct. 28, 2016 on behalf of Giovanni Mogna. dated Feb. 16, 2018 7 pages.
Written Opinion for International Application No. PCT/IB2015/000602 filed on Apr. 30, 2015 on behalf of Giovanni Mogna. dated Aug. 3, 2015. 6 pages.
Iyer C. et al., "Probiotic Lactobacillus reuteri promotes TNF-induced apoptosis in human myeloid leukemia-derived cells by modulation of NF-kB and MAPK signalling" Cellular Microbiciogy Mar. 26, 2008 12 pages.
Krasaekoopt, W., et al., "Evaluation of Encapsulation Techniques of Prob.ioiics for Yoghurt," International Dairy Journal,Vol, 13, p. 3-13.2003. 11 Pages.
Non-Final Office Action for U.S. Appl. No. 16/526,115, filed Jul. 30, 2019 on behalf of Hoppmann-Eitle SRL. dated Oct. 30, 2019. 11 pages.
Office Action for Japanese Application No. 2016-506657 dated May 14, 2019 7 pages (English Summary + Original).
The Journal of the Japanese Association for Infectious Diseases, vol. 62, No. 12, P1105-1110, 1988, (Partial Translation + Japanese Only).
Wikipedia, Budapest Treaty, retrieved on Oct. 10, 2019. 3 pages.
Wolf W. et al., "Safety and Tolerance of Lactobacillus reuteri supplementation to a Population Infected with the Human Immunodeficiency Virus" Food and Chemical Toxicology1998 11 pages.
Yagi A. et al., "Bicactive ingredients of Aloe a review update" Fukuyama University 2002 28 pages (Encifish Abstract + Original).
First Chinese Office Action and Search Report for Chinese Application No. CN201580023472.1 filed on Apr. 30, 2015 on behalf of Giovanni Mogna, dated Oct. 31, 2019 20 pages (English + Original)
Mashkovskii M.D. "Lekarstvennie sredstva", Moscow, "Novaya volna", Izdatel Umerenkov, 2012, p. 12 (Partial English + Original).
Mohamadzadeh M. et al., "Lactobacilli activate human dendritic cells that skew T cells toward T helper 1 polarization",PNAS, No. 8, vol. 102, pp. 2880-2885,Feb. 22, 2005 6 pages.
Office Action for Japanese Application No. 2016-566716, dated May 14, 2019. 11 pages (English Summary + Original).
Ren D. "Research on Adhesion and Immunoregulation of Probiotic Lactobacillus ",Chinese Doctoral Dissertations Full text Database, Basic ScienceVolume, No. 8, 2013, Item A006 259,Aug. 15, 2013 22 pages (English + Original).
References Russian Office Action for Russian Application No. RU2016143922/04 filed on Apr. 30, 2015 on behalf of Giovanni Mogna dated Nov. 19, 2019 12 pages (English + Original.).
Notice of Allowance for U.S. Appl. No. 16/526,715, filed Jul. 30, 2019 on behalf of Giovanni Mogna dated Apr. 14, 2020 11 pages.
Fasseas M. et al., "Effects of Lactobacillus salivarius, Lactobacillus reuteri, and Pediococcus acidilactici on the nematode Caenorhabditis elegans include possible antitumor activity" Appl Microbiol Biotechnol, pp. 2109-2118 2013.
Japanese Office Action for JP Application No. 2016566657 filed on Apr. 30, 2015 on behalf of Giovanni Mogna dated Apr. 7, 2020 12 pages (English + Original).
Notice of Allowance for U.S. Appl. No. 16/526,715, filed Jul. 30, 2019 on behalf of Giovanni Mogna dated Aug. 10, 2020 11 pages.
Russian Office Action for RU Application No. 2016143922 filed on Apr. 30, 2015 on behalf of Giovanni Mogna dated Mar. 26, 2020 10 pages (English + Original).
Zhu J. et al., "Lactobacillus salivarius Ren prevent the early colorectal carcinogenesis in 1,2-dirnethylhydrazine-induced rat model" Journal of Applied Microbiology, pp. 208-216 Mar. 2014.
Chinese Decision of Grant for CN Application No. 201580023472 filed on Apr. 30, 2015 on behalf of Giovanni Mogna dated Oct. 12, 2020 5 pages (English + Original).
First Chinese Office Action for CN Application No. 201580024004.6 filed on Apr. 30, 2015 on behalf of Giovanni Mogna dated Dec. 28, 2018 9 pages (English + Original).
Fourth Office Action for Chinese Application No. 201580024004.6 dated Aug. 13, 2020, 10 pages, (Original + English Translation).
Indian Examination Report for IN Application No. 201627035119 filed on Oct. 14, 2016 on behalf of Giovanni Mogna dated Oct. 26, 2020, 3 pages.
Japanese Decision to Grant for JP Application No. 2016566657 filed on Apr. 30, 2015 on behalf of Giovanna Mogna dated Nov. 4, 2020, (English + Original) 5 pages.
Kun C. et al., "Dual role of interferons in tumor immunology" Chinese Journal of Cancer Biotherapy, vol. 20 No. 5, p. 507-514,Oct. 2013, (English Abstract + Original).
Qi Z. et al., "Progress of Research of the Role of IFN-y in HIV Infection", Chinese Journal of AIDS & STD, vol. 10 No. 3,2004, 5 pages (English + Original).
Second Chinese Office Action for CN Application No. 201580023472 filed on Apr. 30, 2015 on behalf of Giovanni Mogna dated May 29, 2020 12 pages (English + Original).
Second Chinese Office Action for CN Application No. 201580024004.6 filed on Apr. 30, 2015 on behalf of Giovanni Mogna dated Sep. 9, 2019, 7 pages, (English + Original).
Thirabunyanon M. et al., "Potential probiotic lactic acid bacteria of human origin induce antiproliferation of colon cancer cells via synergic actions in adhesion to cancer cells and short-chain fatty acid bioproduction." Appl Biochem Biotechnol., vol. 169, Jan. 2013, pp. 511-525.
Third Chinese Office Action for CN Application No. 201580024004 filed on Apr. 30, 2015 on behalf of Giovanni Mogna dated Mar. 12, 2020, 8 pages, (English + Original).
Brazilian Office Action for BR Application No. 112016025626-3 filed on Apr. 30, 2015 on behalf of Giovanni Mogna dated Jan. 27, 2021 5 pages (English + Original).
Japanese Decision to Grant for JP Application No. 2016-566716 filed on Apr. 30, 2015 on behalf of Giovanni Mogna dated Nov. 26, 2020 9 pages (English + Original).
Notice of Allowance for U.S. Appl. No. 16/526,715, filed Jul. 30, 2019, on behalf of Hoffmann-Eitle Srl., dated Mar. 10, 2021. 10 Pages.
Notice of Allowance for U.S. Appl. No. 16/526,715, filed Jul. 30, 2019 on behalf of Giovanni Mogna dated Dec. 8, 2020 9 pages.
Korean Office Action for KR Application No. 10-2016-7033184 filed on Apr. 30, 2015 on behalf of Giovanni Mogna dated Apr. 27, 2021 6 pages (English eq. + Original).

COMPOSITION FOR USE IN TREATING OR PREVENTING VIRAL OR BACTERIAL INFECTIONS IN A SUBJECT UNDERGOING ANTI-TUMOR CHEMOTHERAPY, LEUKEMIA TREATMENT OR AIDS THERAPY COMPRISING L. REUTERI LER03 AND/OR L. SALIVARIUS LS06

CROSS-REFERENCE TO RELATED APPLICATIONS

The present application is the U.S. National Stage of International Patent Application No. PCT/IB2015/000614 filed on Apr. 30, 2015, which, in turn, claims priority to Italian Application No. MI2014A000815 filed on May 5, 2014.

The present invention relates to a composition for use as adjunctive therapy to antitumor chemotherapeutic treatments, acquired immunodeficiency syndrome treatments and leukemia treatments. The composition consists of a mixture comprising or, preferably, consisting of a strain of bacteria *Lactobacillus reuteri* LRE 03 DSM 23879 which is able to strongly stimulate the production of pro-inflammatory cytokines (Th1) interferon INF-gamma, said cytokines exhibit a marked antiviral and/or antibacterial activity, and/or a strain of bacteria *Lactobacillus salivarius* LS06 DSM 26037 which is able to strongly stimulate the dendritic cell production, dendritic cells exhibit a marked antiviral and/or antibacterial activity. Furthermore, said composition can comprise one or more of the following compounds: a bacterial strain being able, when ingested, to produce bacterial exopolysaccharides EPS; and/or a plant polysaccharide such as tara gum; and/or an *Aloe arborescens* gel; and/or a gelling agent such as sodium alginate and/or a highly bioavailable zinc, internalized into a tyndallized bacterial cell.

As regards oncology, the current medical therapy is known to comprise chemotherapy, endocrine therapy, the treatment with immune response modifiers and the treatment with molecular-targeted drugs. The main purpose of antitumor chemotherapy is to kill, at any cell cycle phases, neoplastic cells and thus, reduce both primary tumor and metastasis masses.

It is known that antitumor chemotherapeutic treatments decrease the immune system activity and that a compromised immune system is unable to protect organisms against viral and bacterial infections.

In addition, it is known that chemotherapy (chemo) primarily affects the tumor but, unfortunately, it also causes side-effects on healthy tissues, specifically those with a fast proliferation and turnover, such as esophageal, gastric and intestinal mucosae, resulting in mucositis, nausea, vomiting, diarrhea, nutrient malabsorption and, thus, malnutrition.

Therefore, the common denominator of all chemotherapeutics is: bone marrow toxicity, which, in turn, leads to immunodepression and consequent infections, mainly caused by Gram-negative bacteria and fungi such as *Candida*, gastrointestinal epithelium toxicity and intestinal microflora toxicity (chemotherapeutic antibiotics).

The administration of effective chemotherapy doses without a concomitant therapy able to counteract—of course within certain limits—the adverse effects of chemo, by establishing an adjunctive therapy, would not be possible.

Accordingly, it would be desirable to have a natural and well-tolerated solution able to lessen the adverse effects, typical of a chemotherapeutic treatment.

For this reason, there is still a need for having an adjunctive therapy in order to prevent and/or reduce both symptoms and side effects of chemotherapy being used for the treatment of tumors, specifically the damages to esophageal, gastric and intestinal mucosae, which are usually affected during chemotherapeutic treatments. It is thus essential to have a suitable protection and defense of mucosae such as, for example, esophageal mucosa, gastric mucosa and intestinal mucosa.

Furthermore, there is still a need for having an adjunctive therapy to chemotherapy, being able to act on immune system by stimulating it (immunostimulation), in order to restore its efficacy, since chemotherapy entails a reduction of the immune system efficacy, which leads to body's susceptibility to bacteria and viruses, causing the occurrence of bacterial and viral infections.

Figure 1:
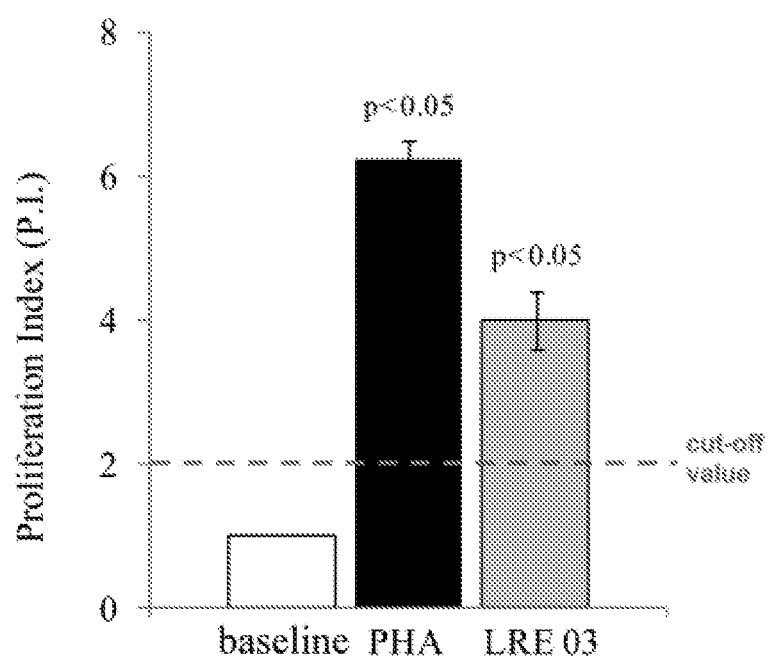
FIG. 1 shows a plot reporting the cell proliferation index (P.I.) of PHA and LRE 03 in comparison to the baseline. The PBMC proliferative response under all the stimulation conditions resulted significantly higher than in absence of stimulation (baseline).

After a long and intensive research activity on a wide group of bacterial strains belonging to different species, the Applicant identified and selected specific bacterial strains able to meet the above-cited needs. It is an object of the present invention:

a bacterial strain belonging to the species *Lactobacillus reuteri*, identified as *Lactobacillus reuteri* LRE03 with deposit number DSM 23879, deposited on 5 Aug. 2010 by Probiotical SpA at DSMZ—Deutsche Sammlung von Mikroorganismen und Zellkulturen GmbH, under the Budapest Treaty, and/or a bacterial strain belonging to the species *Lactobacillus salivarius*, identified as *Lactobacillus salivarius*

LS06 with deposit number DSM 26037, deposited on 6 Jun. 2012 by Probiotical SpA at DSMZ—Deutsche Sammlung von Mikroorganismen und Zellkulturen GmbH, under the Budapest Treaty.

The Applicant found that the strain of bacteria *Lactobacillus reuteri* LRE03 DSM 23879 exhibits a marked antiviral and/or antibacterial activity due to its proven and surprising ability (see experimental part) to stimulate the production of pro-inflammatory cytokines (Th1) interferon INF-gamma. The strain of bacteria *Lactobacillus reuteri* LRE03 DSM 23879 shows a surprising immunostimulatory activity towards the endogenous production of interferon gamma IFN-gamma. The strain of bacteria *Lactobacillus reuteri* LRE03 DSM 23879, selected by the Applicant, exhibits a surprising immunomodulatory activity due to the activation, at mucosal level, of the immune system, exerting an antimicrobial and pro-inflammatory action through the stimulation of pro-inflammatory cytokines (Th1) interferon INF-gamma. Endogenous cytokine production does not cause toxicity, as opposed to the infusion administration of said cytokines, as in the case of exogenous cytokines.

The Applicant also found that the strain of bacteria *Lactobacillus salivarius* LS06 DSM 26037 exhibits a marked antiviral and/or antibacterial activity due to its proven and surprising ability (see experimental part) to stimulate the dendritic cell production. Dendritic cells assist the immune system in protecting organisms from outside attacks of dangerous microorganisms, such as viruses and bacteria.

Finally, the Applicant found that a bacterial strain belonging to the species *Lactobacillus fermentum*, identified as *Lactobacillus fermentum* LF11 with deposit number DSM 19188, deposited on 20 Mar. 2007 by Anidral S.r.l. Company (now Probiotical S.p.A) at DSMZ—Deutsche Sammlung von Mikroorganismen und Zellkulturen GmbH, under the Budapest Treaty, is able to create and maintain an intestinal environment unfavorable to the occurrence, persistence or propagation of a *Candida* infection, in particular against the species *Candida albicans, Candida krusei, Candida glabrata* and *Candida parapsilosis*, frequently occurring in patients treated with chemotherapeutic drugs, due to the consequent chronic dysbiosis condition. In vitro inhibition data strongly suggest that the mechanism of action of the strain *L. fermentum* LF11 DSM19188 is at least partially based on specific molecules other than organic acids, such as bacteriocins, extracellular proteins or hydrogen peroxide.

It is an object of the present invention a (i) mixture of bacteria comprising or, alternatively, consisting of: a strain of bacteria *Lactobacillus* muted LRE03 DSM 23879, and/or a strain of bacteria *Lactobacillus salivarius* LS06 DSM 26037, and/or a strain of bacteria *Lactobacillus fermentum* LF11 DSM 19188.

In an embodiment, said mixture (i) comprises or, alternatively, consists of:
a strain of bacteria *Lactobacillus reuteri* LRE03 DSM 23879, or
a strain of bacteria *Lactobacillus salivarius* LS06 DSM 26037, or
a strain of bacteria *Lactobacillus fermentum* LF11 DSM 19188, for use as antiviral and/or antibacterial agent in individuals undergoing antitumor chemotherapeutic treatments, acquired immunodeficiency syndrome treatments and leukemia treatments or, alternatively, for use in the protection of gastric, esophageal and intestinal mucosae in individuals undergoing antitumor chemotherapeutic treatments, acquired immunodeficiency syndrome treatments and leukemia treatments.

In another embodiment, the (i) mixture of bacteria comprises or, alternatively, consists of:
a strain of bacteria *Lactobacillus reuteri* LRE03 DSM 23879 and a strain of bacteria *Lactobacillus salivarius* LS06 DSM 26037, in a weight ratio comprised from 1:5 to 5:1, preferably from 1:3 to 3:1, even more preferably from 1:2 to 2:1 or 1:1, or
a strain of bacteria *Lactobacillus reuteri* LRE03 DSM 23879 and a strain of bacteria *Lactobacillus fermentum* LF11 DSM 19188, in a weight ratio comprised from 1:5 to 5:1, preferably from 1:3 to 3:1, even more preferably from 1:2 to 2:1 or 1:1, or
a strain of bacteria *Lactobacillus salivarius* LS06 DSM 26037 and a strain of bacteria *Lactobacillus fermentum* LF11 DSM 19188, in a weight ratio comprised from 1:5 to 5:1, preferably from 1:3 to 3:1, even more preferably from 1:2 to 2:1 or 1:1, for use as antiviral and/or antibacterial agent in individuals undergoing antitumor chemotherapeutic treatments, acquired immunodeficiency syndrome treatments and leukemia treatments or, alternatively, for use in the protection of gastric, esophageal and intestinal mucosae in individuals undergoing antitumor chemotherapeutic treatments, acquired immunodeficiency syndrome treatments and leukemia treatments.

In still another embodiment, the (i) mixture of bacteria comprises or, alternatively, consists of a strain of bacteria *Lactobacillus reuteri* LRE03 DSM 23879, a strain of bacteria *Lactobacillus salivarius* LS06 DSM 26037 and a strain of bacteria *Lactobacillus fermentum* LF11 DSM 19188 in a weight ratio comprised among 3:2:1, 3:1:1, 2:1:1, 2:2:1, 1:1:1, for use as antiviral and/or antibacterial agent in individuals undergoing antitumor chemotherapeutic treatments, acquired immunodeficiency syndrome treatments and leukemia treatments or, alternatively, for use in the protection of gastric, esophageal and intestinal mucosae in individuals undergoing antitumor chemotherapeutic treatments, acquired immunodeficiency syndrome treatments and leukemia treatments.

The (i) mixture of bacteria has a bacterial cell concentration comprised from $1 \times 10^8$ UFC/g of mixture to $1 \times 10^{12}$ UFC/g of mixture, preferably from $1 \times 10^9$ UFC/g of mixture to $1 \times 10^{11}$ UFC/g of mixture. Within the context of the present invention, all the above-described mixtures are referred to, for the sake of brevity, as "the mixture of bacteria or mixtures of bacteria of the present invention".

It is another object of the present invention a pharmaceutical composition or a food composition or a supplement product composition or a medical device composition, which is meant as a substance in compliance with the directive 93/42/EEC definition, hereinafter referred to, for the sake of brevity, as "the composition or compositions of the present invention", said composition comprises or, alternatively, consists of:
(i) a mixture of bacteria of the present invention, as described above, and/or
(ii) a strain of bacteria *Streptococcus thermophilus* ST10 DSM 25246 and a tara gum (a plant polysaccharide), said strain, when ingested, being able to produce in situ exopolysaccharides (EPS), which form, in the presence of tara gum, a so-called "mucoadherent gelling complex", and/or
(iii) a mixture comprising or, alternatively, consisting of a gum, preferably an alginate, or a derivative thereof, and/or a gel, preferably an *Aloe* gel, or a derivative thereof, and/or
(iv) a source of highly assimilable zinc, and/or
(v) one or more food grade or pharma grade excipients and/or additives and/or co-formulants, acceptable by the body.

In an embodiment, which is an object of the present invention, the composition of the present invention comprises or, alternatively, consists of: (i) a mixture of bacteria of the present invention and (v) one or more food grade or pharma grade excipients and/or additives and/or co-formulants, acceptable by the body, said composition being for use as antiviral and/or antibacterial agent in individuals undergoing antitumor chemotherapeutic treatments, acquired immunodeficiency syndrome treatments and leukemia treatments or, alternatively, for use in the protection of gastric, esophageal and intestinal mucosae in individuals undergoing antitumor chemotherapeutic treatments, acquired immunodeficiency syndrome treatments and leukemia treatments.

In another embodiment, which is an object of the present invention, the composition of the present invention comprises or, alternatively, consists of: (i) a mixture of bacteria of the present invention, (ii) a strain of bacteria *Streptococcus thermophilus* ST10 DSM 25246 and a tara gum (a plant polysaccharide), said strain, when ingested, being able to produce in situ exopolysaccharides (EPS), which form, in the presence of tara gum, a so-called "mucoadherent gelling complex" and (v) one or more food grade or pharma grade excipients and/or additives and/or co-formulants, acceptable by the body, said composition being for use as antiviral and/or antibacterial agent in individuals undergoing antitumor chemotherapeutic treatments, acquired immunodeficiency syndrome treatments and leukemia treatments or, alternatively, for use in the protection of gastric, esophageal and intestinal mucosae in individuals undergoing antitumor chemotherapeutic treatments, acquired immunodeficiency syndrome treatments and leukemia treatments. Said mucoadherent gelling complex is able to provide a mechanical barrier effect throughout the gastrointestinal tract. Bacterial exopolysaccharides (EPS) are exopolysaccharides being produced in situ by a strain of bacteria *Streptococcus thermophilus* ST10 DSM 25246. The strain of bacteria *Streptococcus thermophilus* ST10 DSM 25246 was deposited on 19 Sep. 2011 at DSMZ—Deutsche Sammlung von Mikroorganismen and Zellkulturen GmbH, under the Budapest Treaty, by Probiotical S.p.A. The composition of the present invention comprises from $1\times10^8$ to $1\times10^{12}$ of *Streptococcus thermophilus* ST10 DSM 25246 viable cells/g of composition, preferably from $1\times10^8$ to $1\times10^{11}$ of *Streptococcus thermophilus* ST10 DSM 25246 viable cells/g of composition.

In another embodiment, which is an object of the present invention, the composition of the present invention comprises or, alternatively, consists of: (i) a mixture of bacteria of the present invention, (ii) a strain of bacteria *Streptococcus thermophilus* ST10 DSM 25246 and a tara gum (a plant polysaccharide), said strain, when ingested, being able to produce in situ exopolysaccharides (EPS), which form, in the presence of tara gum, a so-called "mucoadherent gelling complex", (iii) a mixture comprising or, alternatively, consisting of a gum, preferably an alginate, or a derivative thereof and/or a gel, preferably an *Aloe* gel, or a derivative thereof and (v) one or more food grade or pharma grade excipients and/or additives and/or co-formulants, acceptable by the body, said composition being for use as antiviral and/or antibacterial agent in individuals undergoing antitumor chemotherapeutic treatments, acquired immunodeficiency syndrome treatments and leukemia treatments or, alternatively, for use in the protection of gastric, esophageal and intestinal mucosae in individuals undergoing antitumor chemotherapeutic treatments, acquired immunodeficiency syndrome treatments and leukemia treatments. Said (iii) mixture comprises or, alternatively, consists of a gum, preferably an alginate, or a derivative thereof and/or a gel, preferably an *Aloe* gel, or a derivative thereof. The alginate, or a derivative thereof, is preferably sodium alginate. The *Aloe* product, or a derivative thereof, is preferably *Aloe arborescens*; preferably in freeze-dried form. The *Aloe arborescens* is preferably in freeze-dried form. In an embodiment the composition of the present invention comprises sodium alginate and freeze-dried *Aloe arborescens* in a weight ratio comprised from 1:50 (alginate: *Aloe*) to 50:1, preferably from 1:30 (alginate: *Aloe*) to 30:1.

Furthermore, the Applicant found that the immune system (IS) activation can be also obtained through a very highly bioavailable zinc, in addition to the action promoted by the strain of bacteria *Lactobacillus reuteri* LRE03 DSM 23879 and/or the strain of bacteria *Lactobacillus salivarius* LS06 DSM 26037. The very high bioavailability is due to the fact that zinc is in the form of zinc internalized into a tyndallized bacterial cell of a bacterial strain belonging to the species *Bifidobacterium lactis*, preferably the strain selected by the Applicant is the strain of bacteria *Bifidobacterium lactis* Bb 1 DSM 17850 deposited at DSMZ on 23 Dec. 2005, which is the object of the European Patent Application No. 08789404, herein incorporated by reference.

Basically, the Applicant found that the highly bioavailable zinc internalized into a tyndallized cell (inactivated cell) is able to activate the immune system (IS), specifically the thymus which is responsible for the production of T-lymphocytes, which produce non-toxic endogenous cytokines, such as interferon-gamma.

In another embodiment, which is an object of the present invention, the composition of the present invention comprises or, alternatively, consists of: (i) a mixture of the present invention, (ii) a strain of bacteria *Streptococcus thermophilus* ST10 DSM 25246 and a tara gum (a plant polysaccharide), said strain, when ingested, being able to produce in situ exopolysaccharides (EPS), which form, in the presence of tara gum, a so-called "mucoadherent gelling complex", (iii) a mixture comprising or, alternatively, consisting of a gum, preferably an alginate, or a derivative thereof and/or a gel, preferably an *Aloe* gel, or a derivative thereof, (iv) a source of highly assimilable and bioavailable zinc in the form of zinc internalized into a tyndallized bacterial cell of a bacterial strain belonging to the species *Bifidobacterium lactis*, said strain is preferably the strain of bacteria *Bifidobacterium lactis* Bb 1 DSM 17850 and (v) one or more food grade or pharma grade additives and/or co-formulants and/or formulation technological ingredients, acceptable by the body, said composition being for use as antiviral and/or antibacterial agent in individuals undergoing antitumor chemotherapeutic treatments, acquired immunodeficiency syndrome treatments and leukemia treatments or, alternatively, for use in the protection of gastric, esophageal and intestinal mucosae in individuals undergoing antitumor chemotherapeutic treatments, acquired immunodeficiency syndrome treatments and leukemia treatments. Said (iv) source of highly assimilable and bioavailable zinc is present as organic zinc in the form of bacterial tyndallized product of the strain *Bifidobacterium lactis* Bb1 DSM 17850 (ProbioZinc®, deposited on 23 Dec. 2005 at DSMZ—Deutsche Sammlung von Mikroorganismen and Zellkulturen GmbH, by BioMan S.r.l. Company (Italy). The bacterial tyndallized product of the strain *Bifidobacterium animalis* ssp. *lactis* Bb1 DSM 17850 is in an amount comprised from 10 to 50 mg/g of composition, preferably 20 mg/g of composition.

All the above-cited compositions of the present invention are effectively applicable for use as adjunctive therapy to antitumor chemotherapeutic treatments, acquired immunodeficiency syndrome treatments and leukemia treatments. Additionally, the compositions of the present invention are effectively applicable for use as adjunctive therapy in order to prevent and/or lessen symptoms and side effects typical of chemotherapy being used for the treatment of tumors, specifically the damages caused to esophageal, gastric and intestinal mucosae, which are usually affected during chemotherapeutic treatments. Finally, the compositions of the present invention are effectively applied for use as adjunctive therapy to the immune system, since chemotherapy entails a reduction of the immune system efficacy, which leads to body's susceptibility to bacteria and viruses, causing the occurrence of bacterial and viral infections.

Ultimately, the composition of the present invention comprises food grade or pharma grade excipients and/or additives and/or co-formulants for allowing the manufacture of pharmaceutical forms as powders, granules, tablets or capsules.

The composition of the present invention comprises from $1 \times 10^8$ to $1 \times 10^{12}$ of bacterial viable cells UFC/g of composition, preferably from $1 \times 10^9$ to $1 \times 10^{11}$ of bacterial viable cells UFC/g of composition. The composition of the present invention is preferably recommended to be administered 1-2 times daily for 4-12 weeks.

The composition of the present invention consists of a suitable amount of tara gum which, due to its gelling and mucoadherent properties, is able to form a hydrogel within few minutes after ingestion, by virtue of its thixotropic properties, thereby creating in the first gastrointestinal tract a mechanical barrier action against the pathogenic microorganism adhesion to the mucosa of the organ, thus reducing the translocation thereof through the gut wall and the consequent risk of adjacent organ infection, which is fundamental when an impairment of the immune system functions occurs. Such a barrier effect is completed and extended throughout the gastrointestinal tract by the simultaneous presence of exopolysaccharides (EPS), being produced in situ by the microorganism *Streptococcus thermophilus* ST10, thereby increasing the viscosity of the surrounding environment through a self-regulating, only mechanical mechanism. The ingestion of said bacterium delivers in the human intestine a source of gelling molecules, thus exerting a fully complementary action to tara gum.

The above-cited mucoadherent gelling complex has an innovative property which has to be taken into account: the plant tara gum is gradually degraded by the resident microbiota during its intestinal transit, thereby progressively reducing its gelling power of mechanical hindrance. The gradual reduction of the plant gum action is effectively counterbalanced by the progressive increase of the release in the intestinal lumen of exopolysaccharides (EPS), which are produced in situ by the bacterial strain *Streptococcus thermophilus* ST10 DSM 25246, which mainly acts in ileum and colon.

Thus, the synergistic combination of tara gum and exopolysaccharides (EPS) being produced in situ ensures the presence of gelling molecules throughout the gastrointestinal tract, maximizing and optimizing the mechanical barrier action of the product. Therefore, the presence, production and retention of the hydrophilic gel in the lumen of the organ can be considered, for the first time, really complete, with a first area wherein the action of the plant gum is maximum and a second area wherein the action of exopolysaccharides (EPS) being produced in situ is maximum.

Due to the presence of freeze-dried *Aloe arborescens* (Alagel™) (for example 1.5 gram/dose) and sodium alginate (for example 50 mg/dose), two components with gelling activity, the composition of the present invention is able to ensure a mechanical barrier effect for protecting esophageal, gastric and intestinal mucosae. Furthermore, sodium alginate has a mechanical hindrance activity against gastroesophageal reflux, as well as a physical protection activity against esophagitis and gastritis. In this way, the combination of *Aloe arborescens* and sodium alginate is able to make the side effects of a chemotherapeutic treatment more tolerable in individuals with a tumor disease. Moreover, the *Aloe arborescens* product, besides the action of physical protection of esophageal, gastric and intestinal mucosae, is able to lessen the adhesive capabilities of pathogenic strains through a physical-mechanical hindrance, with particular reference to flagellated microorganisms, both at esophageal and gastrointestinal level. The *Aloe* product is also able to reduce the gastric and intestinal permeability, thereby contributing to the restoration of the physiological barrier effect of such an organ and to synergistically act with tara gum and exopolysaccharides (EPS) for lowering the risk of bacterial translocation from intestine. Moreover, *Aloe arborescens* has an anti-inflammatory activity, thus offering a further protection at mucosal level.

In light of its overall mechanism of action, the composition of the present invention is able to make the side effects, especially bacterial infections, of a chemotherapeutic treatment more tolerable in individuals with a tumor disease.

In addition, the presence, in the composition of the present invention, of a (i) mixture of the present invention (having a bacterial cell concentration comprised from $1 \times 10^8$ UFC/g of mixture to $1 \times 10^{12}$ UFC/g of mixture, preferably from $1 \times 10^9$ UFC/g of mixture to $1 \times 10^{11}$ UFC/g of mixture) comprising or, alternatively, consisting of:

- a strain of bacteria *Lactobacillus reuteri* LRE03 DSM 23879, or
- a strain of bacteria *Lactobacillus salivarius* LS06 DSM 26037, or
- a strain of bacteria *Lactobacillus fermentum* LF11 DSM 19188, or
- a strain of bacteria *Lactobacillus reuteri* LRE03 DSM 23879 and a strain of bacteria *Lactobacillus salivarius* LS06 DSM 26037, in a weight ratio comprised from 1:5 to 5:1, preferably from 1:3 to 3:1, even more preferably from 1:2 to 2:1 or 1:1, or
- a strain of bacteria *Lactobacillus reuteri* LRE03 DSM 23879 and a strain of bacteria *Lactobacillus fermentum* LF11 DSM 19188, in a weight ratio comprised from 1:5 to 5:1, preferably from 1:3 to 3:1, even more preferably from 1:2 to 2:1 or 1:1, or
- a strain of bacteria *Lactobacillus salivarius* LS06 DSM 26037 and a strain of bacteria *Lactobacillus fermentum* LF11 DSM 19188, in a weight ratio comprised from 1:5 to 5:1, preferably from 1:3 to 3:1, even more preferably from 1:2 to 2:1 or 1:1, or
- a strain of bacteria *Lactobacillus reuteri* LRE03 DSM 23879, a strain of bacteria *Lactobacillus salivarius* LS06 DSM 26037 and a strain of bacteria *Lactobacillus fermentum* LF11 DSM 19188 in a weight ratio comprised among 3:2:1, 3:1:1, 2:1:1, 2:2:1, 1:1:1; ensures a strengthening of the above-cited barrier effect by a mechanism being supplementary to that of mucoadherent gelling complex, *Aloe arborescens* and sodium alginate.

Indeed, the strain *L. reuteri* LRE03 DSM 23879 is able to significantly stimulate the endogenous production of interferon-gamma (IFN-γ). The ability of the strain *L. reuteri* LRE03 DSM 23879 to induce the release of cytokines, in particular interferon-gamma INF-gamma, by the primary cells of immune system was quantified by co-incubation thereof with PBMCs (Peripheral Blood Mononuclear Cells) isolated from peripheral blood of healthy adult individuals. The results showed a stimulation of IFN-gamma secretion with a concentration of 480 pg/ml, namely 47-fold greater than the control. The IFN-gamma production was assessed in a culture supernatant after 5 days of stimulation relative to non-stimulation conditions (baseline).

Interferon-gamma (IFN-γ) has hindrance properties against viral and bacterial infections, similarly to the other interferons, and non-physiological cell proliferation, which is mediated by changes of cytoskeleton and cell membrane, modulations of oncogene product expression and regulation of the cell differentiation process (protraction of almost all the phases of mitosis both in normal and tumor cells). IFN-γ also shows a pivotal and characteristic immunomodulatory effect, by stimulating the activity of both cells specialized in the body's immune response such as macrophages, monocytes, neutrophils and unspecialized cells such as platelets, endothelial and epithelial cells, fibroblasts and parenchymal cells.

A further strengthening of the barrier effect derived from the composition of the present invention and mediated by *Aloe* and sodium alginate, is ensured by the presence of a suitable amount of highly assimilable zinc (2 mg/dose), internalized by the microorganism *Bifidobacterium lactis* Bb1. The highly bioavailable (internalized) zinc is in the form of tyndallized (inactivated) cell. This form of zinc is very bioavailable and, thus, more easily assimilable by the organism. The zinc ion, being bioavailable and readily assimilable by the organism, plays a pivotal role and an action towards thymus, which is responsible for the formation/production of lymphocytes.

The strain of bacteria *Bifidobacterium* lactic Bb 1 DSM 17850 was deposited at DSMZ on 23 Dec. 2005, by BioMan S.r.l. Company (Italy). Indeed, the strain of bacteria *Bifidobacterium* lactic Bb 1 DSM 17850 is able to accumulate zinc inside the cell during its growth in a liquid culture medium. The dietary zinc accumulated inside the cell (ProbioZinc®) has an assimilability 17-fold greater than zinc gluconate and 31.5-fold greater than zinc sulfate, as shown in an in vitro study carried out on Caco-2 cells in a Transwell system. The high assimilability of the trace element zinc allows to effectively counterbalancing deficiency conditions even at very low dosages. Furthermore, zinc is known for playing an important role as regards the immune system, specially the thymus, the organ where the production of T-lymphocytes takes place which, when differentiate to CD4+T-lymphocytes (helper T-lymphocytes), secrete a series of cytokines such as IL-12 and IFN-γ. Said zinc mechanism of action is synergistic with that of the strain *L. reuteri* LRE03 DSM 23879.

In addition to the above, the strains *L. reuteri* LRE03 DSM 23879 and *L. fermentum* LF11 DSM 19188 mediate the strengthening of the barrier effect for protecting the gastrointestinal mucosae, mediated by the gelling complex, *Aloe* and sodium alginate, through an hindrance action against Gram-negative bacteria, mainly the strain *L. fermentum* LF11 DSM 19188 directly acts against coliform bacteria, *E. coli* and fungi of the genus *Candida*. Microorganisms with a marked barrier action against potential Gram-negative pathogens, with particular reference to the species *Escherichia coli*, *Enterobacter cloacae* and *Klebsiella pneumoniae*, which are coliform bacteria that may bring about even severe infections of the gastrointestinal tract in individuals undergoing chemotherapy were selected. Following to this research activity, the strain *L. fermentum* LF11 DSM 19188 was successfully selected.

Additionally, the strain *L. fermentum* LF11 DSM 19188 is also able to establish and retain a barrier effect against yeasts of the genus *Candida*, as demonstrated in particular towards the species *Candida albicans*, *Candida krusei*, *Candida glabrata* and *Candida parapsilosis*. Specifically, the strain *L. fermentum* LF11 DSM 19188 is able to create and maintain an intestinal environment unfavorable to the occurrence, persistence or propagation of a *Candida* infection, frequently occurring in patients treated with chemotherapeutic drugs, as a consequence and expression of the resultant chronic dysbiosis condition.

In vitro inhibition data strongly suggest that the mechanism of action of the strain *L. fermentum* LF11 DSM 19188 is at least partially based on specific molecules other than organic acids, such as bacteriocins, extracellular proteins or hydrogen peroxide.

Interestingly, the components of the composition being object of the present invention having mechanical activity, primarily act by decreasing the adhesive properties of pathogenic strains via a physical-mechanical hindrance, with particular reference to flagellated microorganisms, whereas the strains of bacteria *L. reuteri* LRE03 DSM 23879, *Lactobacillus salivarius* LS06 DSM 26037 and *L. fermentum* LF11 DSM 19188 exert an adjunctive effect to the above-cited hindrance against pathogens (virus and bacteria and yeasts) which become unable to adhering to the mucosal surface, thus remaining in the gastrointestinal lumen.

In light of the above, the mechanism of action of the composition being object of the present invention is the establishment and maintenance of a mechanical barrier effect for the physical protection of esophageal, gastric and intestinal mucosae, also reducing the adhesive capability of pathogenic strains, with particular reference to flagellated strains. Furthermore, the mechanical barrier effect of the product is able to restore a physiological permeability of the intestinal mucosa, typically increased during a chemotherapeutic treatment.

The strengthening effects of the primary barrier effect are the stimulation of endogenous secretion of cytokines able to counteract viral infections and non-physiological cell proliferation, as well as the synthesis of specific molecules with antibacterial and anti-*Candida* activity, thereby providing a further protection to individuals being treated with antitumor chemotherapeutic drugs.

In light of its overall mechanism of action, the composition being object of the present invention is effectively applied for use as adjunctive therapy in individuals with tumor diseases and undergoing chemotherapy, as well as in antiretroviral treatments in individuals with Acquired Immunodeficiency Syndrome (AIDS) and in leukemia treatments.

Experimental Part

The Applicant tested the immunomodulatory properties of the strain of bacteria *Lactobacillus reuteri* LRE 03 (ID1777) DSM 23879, as described below.

Specifically, the investigation was conducted after different times of stimulation, so that to analyze both cytokines involved in innate immunity and those responsible for acquired immunity.

a) Bacterial Cultures and Growth Conditions

Firstly, bacterial cultures of the strain of bacteria *Lactobacillus reuteri* LRE 03 DSM 23879 were prepared under specific growth conditions. The strain was cultured in Man Rogosa Sharpe (MRS) medium, in a thermostatic bath at 37° C. As regards the immunomodulatory experiments, after a growth period of approximately 16 hours, bacteria were subcultured for 6 hours, under the above-cited conditions, in order to reach the exponential growth phase. Then, they were washed twice with sterile phosphate-buffered saline (PBS, pH 7.2); the physiological status and the number of cells were determined with a cytofluorimetric technique by using the commercial kit "Cell Viability Kit with liquid beads", marketed by Becton Dickinson Company, following the manufacturers instructions. The cells were thus brought to the optimal concentration established in preliminary experiments and used in subsequent tests.

b) Peripheral Blood Mononuclear Cell Separation

Next, peripheral blood mononuclear cells were separated. The peripheral blood mononuclear cells (PBMC) were separated by density gradient centrifugation. For this aim, 20 ml of "buffy coat" of healthy donors from the Immuno-transfusion Service of Ospedale di Borgomanero (Italy) were used for each experiment, thus obtaining an average yield of $200 \times 10^6$ PBMC/buffy. The amount of separated cells was determined by cell count in Burker's chambers, using Turk's dye, which allows to discriminating between mononuclear and polymorphonuclear cells. Cells were brought to a concentration of $2 \times 10^6$ cells/ml in RPMI-1640 growth medium (Invitrogen), supplemented with 10% heat inactivated Bovine fetal serum (FCS, Gibco), 1% glutamine and 25 mM Hepes.

c) PBMC Stimulation

Next, the peripheral blood mononuclear cells (PBMC) were stimulated with the bacterial strain. After separation, PBMCs were stimulated with the bacterial strain for 1 and 5 days. The internal controls for each experiment were as follows:

Negative control: PBMCs alone 1 day control: PBMCs stimulated with 1 µg/ml Lipopolysaccharide (LPS; *Escherichia coli*, serotype 055:B5, Sigma Chemicals Co., St. Louis, Mo.).

5 days control: PBMCs stimulated with 1 µg/ml Phytohaemagglutinin (PHA-P; Sigma Chemicals Co., St. Louis, Mo.).

At the different times of analysis, cultures were centrifuged at 1500 rpm for 10 minutes. Supernatants were taken and stored at $-20°$ C. until analysis. The cells were used for subsequent tests.

d) Cell Proliferation Analysis

Then, the cell proliferation analysis was performed. Cell proliferation was assessed with a cytofluorimetric technique by using the bromodeoxyuridine (BrdU) nuclear labeling protocol. This method was developed as alternative to the more traditional radiolabeling system with tritiated thymidine. Particularly, cell cultures were added with a mixture of 5-bromo-2'-deoxyuridine (BrdU) and 2'-deoxycytidine (dC), either at 20 µM final concentration. Following to 16-hour incubation at 37° C. under humidified atmosphere, 5% $CO_2$, the cell proliferation was analyzed by a cytofluorimetric technique. The culture supernatants were harvested and stored at $-20°$ C. until analysis. Following to fixation and cell wall permeabilization, the cellular DNA was labeled with anti-BrdU FITC-conjugated monoclonal antibody (mAb) (Becton Dickinson). The cells were analyzed within 24 hours from their preparation by using a cytofluorimeter FACScalibur from Becton Dikinson Company and the analysis program CellQuest.

Results were expressed as cell proliferation index (P.I.), being calculated as ratio of the percentage of proliferating cells in the presence of stimulus and the percentage of the same in the absence of stimulation. A P.I. value greater than 2 was considered acceptable (cut-off value). In all the experiments, stimulation with the mitogen (PHA) as control always resulted greater than the cut-off value, confirming that PBMCs were viable and with proliferative capability.

e) Analysis of Molecules Characterizing Individual Cell Subpopulations

Next, the analyses of molecules characterizing the individual cell subpopulations were performed. As regards the immunophenotypic characterization, the cells were incubated for 30 minutes in the dark, with different combinations of the following monoclonal antibodies (mAb) conjugated to fluorescein isothiocyanate (FITC), phycoerythrin (PE) or peridinin chlorophyll protein (PerCP): CD3, CD4, CD8, CD14, CD16, CD19, CD20, CD56, HLA-DR. After incubation, the samples were washed, fixed with a solution containing 1% paraformaldehyde and stored at 4° C. Within 24 hours from preparation, the samples were analyzed by a cytofluorimeter FACScalibur, the cells being selected so that to exclude contaminant cellular debris from analysis.

f) Cytokine Dosage

Next, the cytokine dosage was performed. Cytokine concentration in the culture supernatants was determined by E.L.I.S.A. assay (Enzyme-Linked Immunoabsorbent Assay). Specifically, for cytokine (IL-4, IL-10, IFN-γ and IL-12p70) dosage, the kits "Human ELISA Ready-SET-Go" from eBioscence Company, San Diego Calif. were used.

g) Statistical Analysis

A statistical analysis by using the paired Student's t test was performed. A p<0.05 value was considered significant.

Results i) The proliferative response induced by the strain of bacteria *Lactobacillus reuteri* LRE 03 DSM 23879 was determined. In vitro analysis of cell proliferation is a very useful biological parameter for investigating the immune system functioning. In order to analyze whether the tested bacterial strain could affect the induction of lymphocyte proliferation, peripheral blood mononuclear cells (PBMC) were stimulated with the bacterial strain *Lactobacillus reuteri* LRE 03 DSM 23879. Phytohaemagglutinin (PHA), which is a mitogenic stimulus able to induce T-lymphocyte polyclonal proliferation, was used as positive control. PBMCs were separated from peripheral venous blood samples of 4 healthy male donors, average age of 40 years (range 21-52 years), from the Transfusion Service of Ospedale S. S. Trinità, Borgomanero (Novara).

As shown in FIG. 1, wherein the cell proliferation index (P.I., see the above-described methods) is reported, the PBMC proliferative response under all the stimulation conditions resulted significantly higher than in absence of stimulation (baseline).

In FIG. 1, the Mean±standard error of the mean (S.E.M.) of 4 independent experiments is shown. The statistical significance was calculated by using the Student's t test. p<0.05 values have to be considered statistically significant, as compared to the baseline (non-stimulated PBMCs).

ii) The effects of the bacterial strain *Lactobacillus reuteri* LRE 03 DSM 23879 on the different cell subpopulations were assessed. In order to detect which cell subpopulations were induced to proliferate following to stimulation with the tested probiotic strain, a multiparametric flow cytometry analysis was performed. The subsequent figures (FIG. 2 and FIG. 3) show the percentage of the main cell subpopulations involved both in natural and acquired immune response.

iia) Natural Immunity. After one day, the stimulation with the bacterial strain *Lactobacillus reuteri* LRE 03 (DSM 23879) caused a change in total dendritic cell percentage (Lineage-/HLA-DR+).

Figure 2:
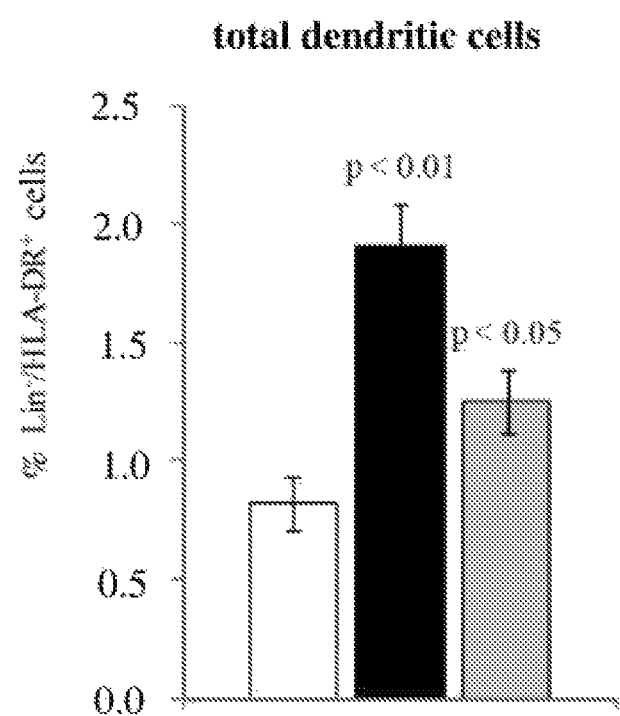
FIG. 2 shows a plot reporting the percentage of total dendritic cell in PHA and LRE 03 relative to the baseline.

In FIG. 2, the proliferative response Mean±S.E.M. of 4 independent experiments is shown. The statistical significance was calculated by using the Student's t test. p<0.05 values have to be considered statistically significant, as compared to the baseline (non-stimulated PBMCs).

iib) Acquired Immunity. After five days, the stimulation with the bacterial strain *Lactobacillus reuteri* LRE 03 DSM 23879 caused a significant increase in helper T-lymphocytes (CD3+/CD4) percentage.

Figure 3:
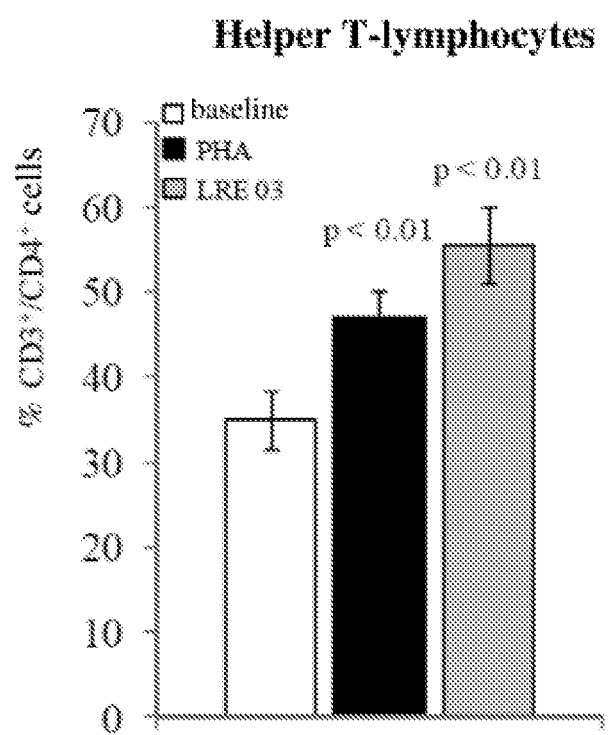
FIG. 3 shows a plot reporting the percentage of helper T-lymphocytes in PHA and LRE 03 relative to the baseline.
Figure 4:
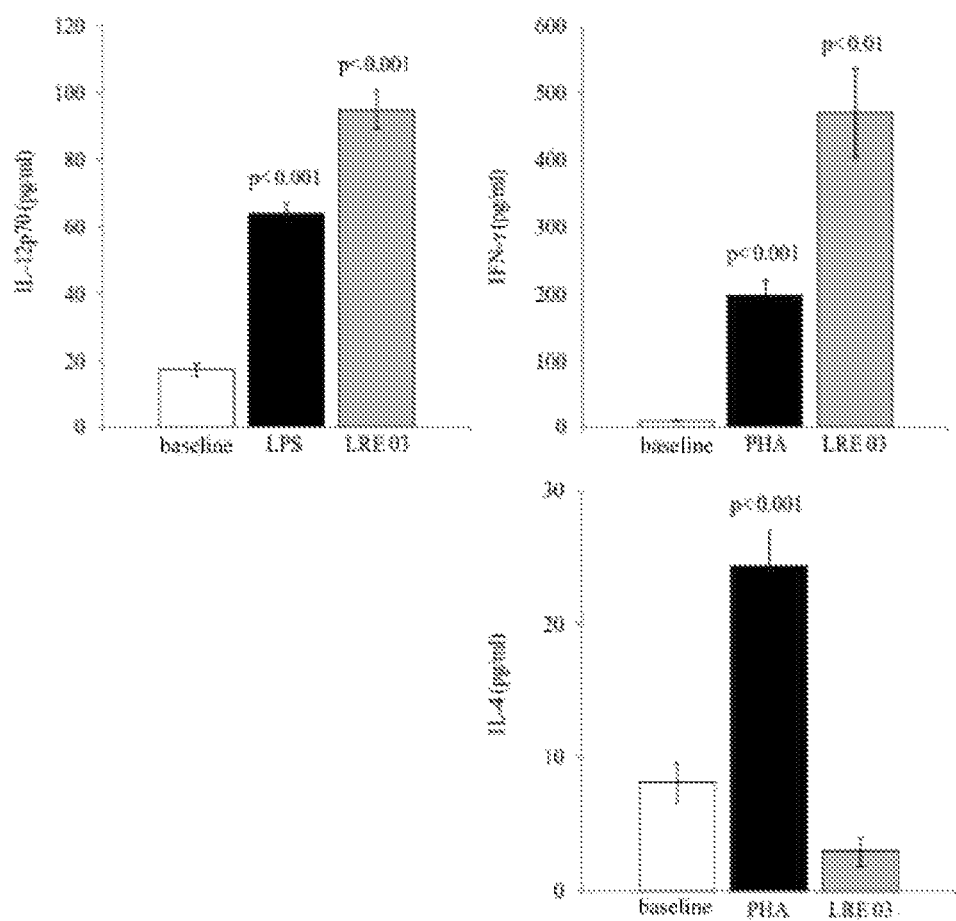
FIG. 4 shows three plot reporting the amount of cytokine IL-12p70, IFN-65 and IL-4 being relased in PHA, LPS and and LRE 03 relative to the baseline.

In FIG. 3, the Mean±S.E.M. of 12 independent experiments is shown. The statistical significance was calculated by using the Student's t test. p<0.05 values have to be considered statistically significant, as compared to the basal condition (non-stimulated PBMCs).

iii) Cytokine secretion. The different spectrum of cytokines secreted by cell subpopulations involved in immune responses plays a pivotal role in selecting the effector system to be used in response to a specific antigenic stimulus. T-lymphocytes represent the main effector and regulatory cells of cell-mediate immunity. In response to an antigen or pathogenic agent, T-cells synthesize and secrete a variety of cytokines required for growth and differentiation and as activating factors of other immunocompetent cells. In order to investigate whether the tested bacterial strain would induce a different cytokine secretion by PBMCs, said cells were activated for 1 and 5 days. The amount of cytokines (IL-12p70, IFN-γ and IL-4) being released in the culture supernatants was measured by E.L.I.S.A. assay.

iv) Cytokines with predominantly pro-inflammatory action. The induction of cytokines IL-12p70 and IFN-γ, as main representatives of cytokines with predominantly pro-inflammatory action was assessed. As shown in FIG. 4, the bacterial strain *Lactobacillus reuteri* LRE 03 (DSM 23879) is able to induce a significant increase of both the tested cytokines, relative to basal conditions.

v) Cytokines with predominantly immunoregulatory action. The induction of cytokines IL-4, as main representatives of cytokines with predominantly immunoregulatory action was assessed. As shown in FIG. 4, the tested bacterial strain *Lactobacillus reuteri* LRE 03 (DSM 23879) shown to be able to induce a reduction of cytokine IL-4 secretion, relative to basal conditions.

In FIG. 4 the Mean±S.E.M. of 4 independent experiments is shown. The statistical significance was calculated by using the Student's t test. p<0.05 values have to be considered statistically significant, as compared to the baseline (non-stimulated PBMCs). The production of cytokines IL-12p70 was assessed in culture supernatants after 1 day of stimulation. IFN-γ and IL-4 production was assessed in culture supernatants after 5 days of stimulation.

Figure 5:
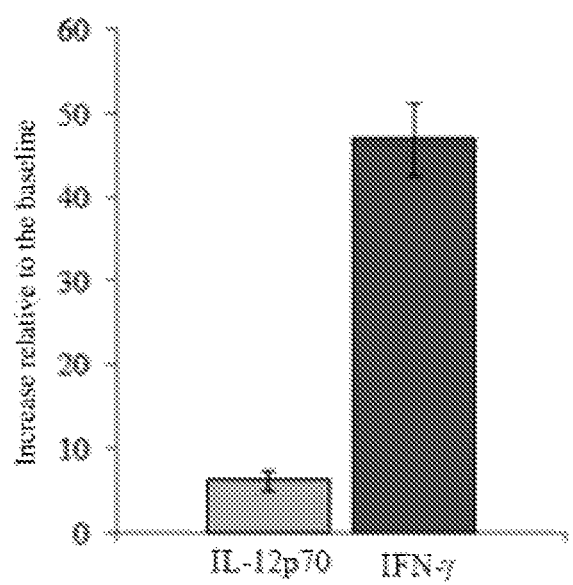
FIG. 5 shows a plot reporting the increase relative to the baseline by LRE 03 strain. The bacterial strain *Lactobacillus reuten* LRE 03 DSM 23879 increased by 6- fold and 47-fold the secretion of cytokine IL-12p70 and cytokine IFN-$\gamma$, respectively, relative to non-stimulation conditions.

Data relative to the dosage of cytokines secreted by PBMCs following to stimulation with the bacterial strain *Lactobacillus reuteri* LRE 03 DSM 23879 underlined the capability of the strain itself to significantly increase pro-inflammatory cytokines. Specifically, the bacterial strain *Lactobacillus reuteri* LRE 03 DSM 23879 increased by 6-fold and 47-fold the secretion of cytokine IL-12p70 and cytokine IFN-γ, respectively, relative to non-stimulation conditions (baseline, FIG. 5).

Considering the marked ability of the bacterial strain *Lactobacillus reuteri* LRE 03 DSM 23879 to stimulate the cytokine IFN-γ secretion, the results of the present study were compared to those obtained from experiments with other bacterial strains, all belonging to Probiotical S.p.A. collection. Specifically, the increase relative to baseline was compared, namely the fold change of the IFN-γ amount, relative to non-stimulation conditions (baseline).

As shown in table 1, the bacterial strain *Lactobacillus reuteri* LRE 03 (DSM 23879) resulted the best IFN-γ inducing agent relative to both strains of the same species and strains of different species, all belonging to the genus *Lactobacillus*.

In Table 1, the increase of cytokine IFN-γ induced by stimulation with different lactobacilli and bifidobacteria, compared to the baseline, is shown.

Experimental Part

The Applicant tested the immunomodulatory properties of the bacterial strain *Lactobacillus salivarius* LS 06 DSM 26037, as described below.

Specifically, the immunomodulatory properties towards total circulating dendritic cells of the probiotic strain *Lactobacillus salivarius* LS 06 DSM 26037, previously characterized from both the microbiological and molecular point of views, were assessed. In particular, after 24 hours of stimulation, a multiparametric flow cytometry analysis, by selecting the DCs in peripheral blood mononuclear cells from healthy adults donors, was carried out.

a) Bacterial Cultures and Growth Conditions

The strain was cultured in Man Rogosa Sharpe (MRS) medium, in a thermostatic bath at 37° C. As regards the immunomodulatory experiments, following to a growth period of approximately 16 hours, the bacteria were subcultured for 6 hours, under the above-cited conditions, in order to reach the exponential growth phase. Thus, they were washed twice with sterile phosphate-buffered saline (PBS, pH 7.2); the physiological status and the number of cells were determined with a cytofluorimetric technique by using the commercial kit "Cell Viability Kit with liquid beads", marketed by Becton Dickinson Company, following the manufacturer's instructions. The cells were then brought to the optimal concentration established in preliminary experiments and used in subsequent tests.

b) Peripheral Blood Mononuclear Cell Separation

Peripheral blood mononuclear cells (PBMC) were separated by density gradient centrifugation. For this aim, 20 ml of "buffy coat" of healthy donors from the Immuno-transfusion Service of Ospedale di Borgomanero were used for each experiment, thereby obtaining an average yield of 200×10$^6$ PBMC/buffy. The amount of separated cells was determined by cell count in Burker's chambers, by using Turk's dye, which allows to discriminating between mononuclear cells and polymorphonuclear cells. The cells were brought to a concentration of 2×10$^6$ cells/ml in RPMI-1640 growth medium (Invitrogen), supplemented with 10% heat inactivated Bovine fetal serum (FCS, Gibco), 1% glutamine and 25 mM Hepes.

c) PBMC Stimulation

After separation, PBMCs were stimulated for 24 hours with the bacterial strain. The internal controls for each experiment were as follows: Negative control: PBMCs alone; 1 day control: PBMCs stimulated with 1 μg/ml Lipopolysaccharide (LPS; *Escherichia coli*, serotype 055:B5, Sigma Chemicals Co., St. Louis, Mo.).

After stimulation, the cultures were centrifuged at 1500 rpm for 10 minutes. Then the supernatant was discharged and the cells used for subsequent tests.

d) Total Dendritic Cells Analysis

As regards the immunophenotypic characterization, cells were incubated for 30 minutes in the dark with different combinations of the following monoclonal antibodies (mAb) conjugated to fluorescein isothiocyanate (FITC) or peridinin chlorophyll protein (PerCP): CD3, CD14, CD16, CD19, CD20, CD56 and HLA-DR. After incubation, the samples were washed, fixed with a solution containing 1% paraformaldehyde and stored at 4° C. Within 24 hours from preparation, the samples were analyzed by a cytofluorimeter FACScalibur, the cells being selected so that to exclude contaminant cellular debris from analysis.

e) Statistical Analysis

A statistical analysis by using the paired Student's t test was performed. A p<0.05 value was considered significant.

Results: Bacterial Strain Effect on Dendritic Cells

In order to determine the effect of the tested probiotic strain to the dendritic cell modulation, a multiparametric flow cytometric analysis was carried out.

Figure 6:
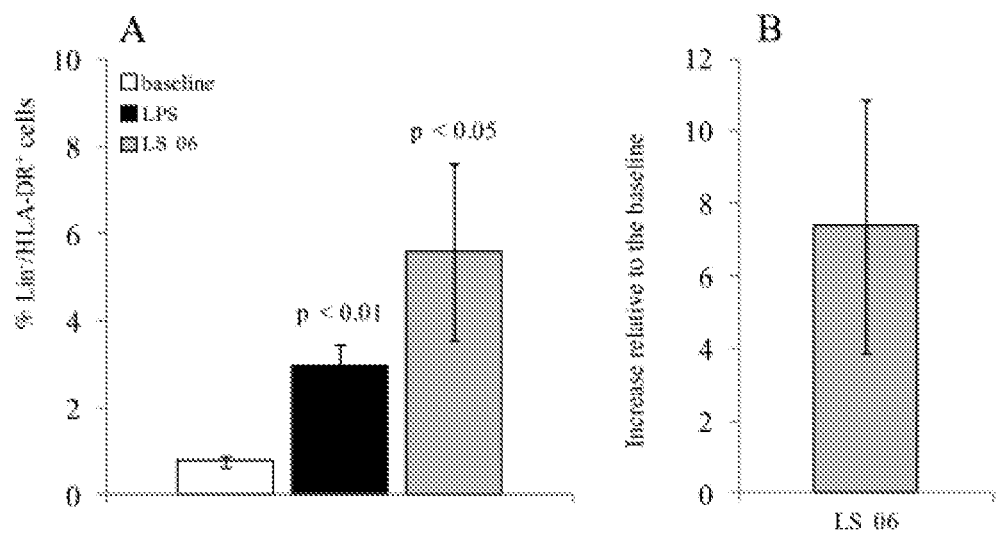
FIG. 6 shows two plots reporting in panel A te increase of total dendritic cell (Lineage-/HLA-DR+) percentage induced by the strain LS 06 compared to the baseline and LPS and in panel B the increase relative to the baseline by LS 06. In particular, the bacterial strain *L. salivarius* LS 06 (DSM 26037) increased by 7- fold the percentage of total dendritic cells, relative to non-stimulation conditions (baseline) (panel B).

As shown in FIG. 6A, after 24 hours, the stimulation with the strain LS 06 induced a significant increase of total dendritic cell (Lineage-/HLA-DR+) percentage.

Specifically, the bacterial strain *L. salivarius* LS 06 (DSM 26037) increased by 7-fold the percentage of total dendritic cells, relative to non-stimulation conditions (baseline, FIG. 6B).

In FIG. 6B, the Mean±S.E.M. of 12 independent experiments is shown. The statistical significance was calculated by using the Student's t test. p<0.05 values have to be considered statistically significant, as compared to the baseline (non-stimulated PBMCs).

In Table 2, the increase of dendritic cells induced by stimulation with different lactobacilli and bifidobacteria, relative to the baseline, is shown.

CONCLUSIONS

Data demonstrated that the bacterial strain *L. salivarius* LS 06 induced a significant increase of total DC percentage, relative to the standard basal conditions. In particular, the bacterium LS 06 increased by 7-fold the total DC percentage.

The intestinal colonization by bacteria capable to modulating the dendritic cells, such as the strain *L. salivarius* LS 06 being characterized in the present study, is a very important factor in diseases characterized by an immunological imbalance.

TABLE 1

| Single strains | Abbreviation | ID | Deposit No. | No. of individuals | IFN-g |
|---|---|---|---|---|---|
| *L. casei* subsp. *paracasei* | LPC 08 | 1696 | DSM 21718 | 8 | 7.83 ± 0.56 |
| *L. fermentum* | LF 11 | 1639 | DSM 19188 | 8 | 8.67 ± 1.05 |
| *L. paracasei* | LPC 00 | 1076 | LMG P-21380 | 8 | 7.83 ± 0.56 |
| *L. paracasei* | LPC 00 | 1076 | LMG P-21380 | 4 | 8.06 ± 0.95 |
| *L. plantarum* | LP 09 | 1837 | DSM 25710 | 4 | 22.29 ± 4.09 |
| *L. pentosus* | LPS 01 | 1702 | DSM 21980 | 8 | 19.54 ± 1.68 |
| *L. reuteri* | LRE 01 | 1775 | DSM 23877 | 4 | 2.79 ± 0.61 |
| *L. reuteri* | LRE 03 | 1777 | DSM 23879 | 4 | 47.02 ± 4.38 |
| *L. rhamnosus* | LR 05 | 1602 | DSM 19739 | 10 | 4.16 ± 1.06 |
| *L. salivarius* | LS 06 (L166) | 1727 | DSM 26037 | 4 | 4.95 ± 0.92 |
| *L. salivarius* | DL V8 | 1813 | DSM 25545 | 4 | 2.74 ± 0.57 |
| *B. animalis* subsp *lactis* | BS 01 | 1195 | LMG P-21384 | 10 | 6.84 ± 0.81 |
| *Bifidobacterium longum* | DL BL07 | 1820 | DSM 25669 | 4 | 15.25 ± 4.01 |
| *Bifidobacterium longum* | DL BL08 | 1823 | DSM 25670 | 4 | 8.95 ± 1.77 |
| *Bifidobacterium longum* | DL BL09 | 1821 | DSM 25671 | 4 | 12.01 ± 2.75 |
| *Bifidobacterium longum* | DL BL10 | 1824 | DSM 25672 | 4 | 11.35 ± 2.09 |
| *Bifidobacterium longum* | DL BL11 | 1825 | DSM 25673 | 4 | 11.85 ± 3.78 |
| *Bifidobacterium longum* | BL01 | 1239 | None | 4 | 21.9 ± 4.67 |
| *Bifidobacterium longum* | BL02 | 1295 | None | 4 | 20.84 ± 0.89 |
| *Bifidobacterium longum* | BL03 | 1152 | DSM 16603 | 4 | 24.44 ± 5.45 |
| *Bifidobacterium longum* | BL04 | 1740 | DSM 23233 | 4 | 19.11 ± 5.38 |
| *Bifidobacterium longum* | W11 | 1114 | None | 4 | 26.01 ± 7.40 |
| *Bifidobacterium longum* | W11 wt | 1161 | None | 4 | 27.42 ± 6.78 |
| *Bifidobacterium longum* | PCB133 | 1687 | DSM 24691 | 4 | 29.09 ± 8.25 |
| *Bifidobacterium longum* | BL05 | 1352 | DSM 23234 | 4 | 14.94 ± 2.28 |
| *Bifidobacterium longum* | BL06 | no ID | DSM 24689 | 4 | 31.90 ± 3.96 |
| *L. acidophilus* | LA02 | 1688 | DSM 21717 | 8 | 4.91 ± 0.70 |
| *L. deldrueckii* subsp. *delbrueckii* | LDD01 | 1391 | DSM 22106 | 8 | 6.46 ± 0.92 |
| *L. fermentum* | LF09 | 1462 | DSM 18298 | 8 | 0.80 ± 0.15 |
| *L. fermentum* | LF10 | 1637 | DSM 19187 | 8 | 4.25 ± 0.4 |
| *L. plantarum* | LP01 | 1171 | LMG P-21021 | 8 | 1.77 ± 0.42 |
| *L. plantarum* | LP02 | 91 | LMG P-21020 | 8 | 4.59 ± 0.59 |
| *L. reuteri* | LRE02 | 1774 | DSM 23878 | 4 | 1.19 ± 0.12 |
| *L. reuteri* | LRE04 | 1779 | DSM 23880 | 4 | 1.72 ± 0.39 |
| *L. reuteri* | DLLRE07 | — | DSM 25683 | 4 | 1.00 ± 0.07 |
| *L. reuteri* | DLLRE08 | 1841 | DSM 25684 | 4 | 0.93 ± 0.06 |
| *L. reuteri* | DLLRE09 | 1842 | DSM 25685 | 4 | 1.22 ± 0.29 |
| *L. rhamnosus* | LR06 | 1697 | DSM 21981 | 10 | 2.64 ± 0.83 |
| *L. salivarius* | LS01 | 1797 | DSM 22775 | 10 | 1.44 ± 0.13 |
| *L. salivarius* | LS04 | — | DSM 24618 | | |
| *L. salivarius* | LS03 | 1382 | DSM 22776 | 10 | 0.72 ± 0.26 |
| *L. salivarius* | DLV1 | 1806 | DSM 25138 | 8 | 1.40 ± 0.13 |
| *L. salivarius* | LS05 (L66) | 1719 | DSM 26036 | 4 | 1.80 ± 0.09 |
| *L. salivarius* | LS02 | 1468 | DSM 20555 | 8 | 1.32 ± 0.67 |
| *B. lactis* | BA05 | 1518 | DSM 18352 | 8 | 1.24 ± 0.08 |
| *B. breve* | BR03 | 1270 | DSM 16604 | 10 | 2.20 ± 0.20 |
| *B. breve* | BR03 | 1270 | DSM 16604 | 8 | 6.92 ± 1.02 |
| *B. pseudolongum* subsp. *globosum* | BPS01 | 1812 | None | 8 | 0.64 ± 0.33 |
| *B. longum* | B1975 | 1742 | DSM 24709 | 4 | 2.99 ± 0.71 |

TABLE 2

| Single strains | Abbreviation | ID | Deposit No. | No. of individuals | Dendritic cells |
|---|---|---|---|---|---|
| L. fermentum | LF 11 | 1639 | DSM 19188 | 8 | 0.98 ± 0.12 |
| L. paracasei | LPC 00 | 1076 | LMG P-21380 | 8 | 1.47 ± 0.24 |
| L. pentosus | LPS 01 | 1702 | DSM 21980 | 8 | 1.46 ± 0.28 |
| L. reuteri | LRE 03 | 1777 | DSM 23879 | 4 | 2.11 ± 0.59 |
| L. rhamnosus | LR 05 | 1602 | DSM 19739 | 10 | 1.84 ± 0.29 |
| L. salivarius | LS06 (L166) | 1727 | DSM 26037 | 4 | 7.35 ± 3.52 |
| B. animalis subsp. lactis | BS 01 | 1195 | LMG P-21384 | 10 | 1.32 ± 0.12 |
| L. acidophilus | LA02 | 1688 | DSM 21717 | 8 | 0.76 ± 0.16 |
| L. deldrueckii subsp. delbrueckii | LDD01 | 1391 | DSM 22106 | 8 | 1.14 ± 0.19 |
| L. fermentum | LF09 | 1462 | DSM 18298 | 8 | 1.23 ± 0.12 |
| L. fermentum | LF10 | 1637 | DSM 19187 | 8 | 1.03 ± 0.19 |
| L. plantarum | LP01 | 1171 | LMG P-21021 | 8 | 0.86 ± 0.18 |
| L. plantarum | LP02 | 91 | LMG P-21020 | 8 | 1.27 ± 0.18 |
| L. salivarius | LS01 | 1797 | DSM 22775 | 10 | 3.93 ± 2.01 |
| L. salivarius | LS04 | — | DSM 24618 | | |
| L. salivarius | LS03 | 1382 | DSM 22776 | 10 | 5.96 ± 3.53 |
| L. salivarius | LS02 | 1468 | DSM 20555 | 8 | 3.97 ± 1.80 |
| B. lactis | BA05 | 1518 | DSM 18352 | 8 | 1.34 ± 0.47 |
| B. breve | BR03 | 1270 | DSM 16604 | 10 | 1.83 ± 0.29 |

The invention claimed is:

1. A method to provide an adjunctive therapy to an individual undergoing antitumor chemotherapeutic treatment, acquired immunodeficiency syndrome treatment or leukemia treatment, the method comprising
administering to the individual an antiviral and/or antibacterial composition comprising:
a strain of bacteria belonging to the species *Lactobacillus reuteri* identified as *Lactobacillus reuteri* LRE03 with deposit number DSM 23879, deposited on 5 Aug. 2010 by Probiotical SpA at DSMZ—Deutsche Sammlung von Mikroorganismen und Zellkulturen GmbH, and/or
a strain of bacteria belonging to the species *Lactobacillus salivarius* identified as *Lactobacillus salivarius* LS06 with deposit number DSM 26037, deposited on 6 Jun. 2012 by Probiotical SpA at DSMZ Deutsche Sammlung von Mikroorganismen und Zellkulturen GmbH, thereby providing adjunctive therapy to said individual.

2. The method according to claim 1, wherein said composition further comprises:
a strain of bacteria belonging to the species *Lactobacillus fermentum* identified as *Lactobacillus fermentum* LF11 with deposit number DSM 19188, deposited on 20 Mar. 2007 by Anidral S.r.l. Company (now Probiotical S.p.A) at DSMZ Deutsche Sammlung von Mikroorganismen und Zellkulturen GmbH.

3. The method according to claim 1, wherein said composition has a bacterial concentration from $1\times10^8$ UFC/g to $1\times10^{12}$ UFC/g.

4. The method according to claim 2, wherein said composition comprises:
a strain of bacteria *Lactobacillus reuteri* LRE03 DSM 23879 and a strain of bacteria *Lactobacillus salivarius* LS06 DSM 26037, in a weight ratio from 1:5 to 5:1,
a strain of bacteria *Lactobacillus reuteri* LRE03 DSM 23879 and a strain of bacteria *Lactobacillus fermentum* LF11 DSM 19188, in a weight ratio from 1:5 to 5:1, and
a strain of bacteria *Lactobacillus salivarius* LS06 DSM 26037 and a strain of bacteria *Lactobacillus fermentum* LF11 DSM 19188, in a weight ratio from 1:5 to 5:1.

5. The method according to claim 3, wherein said composition comprises:
a strain of bacteria *Lactobacillus reuteri* LRE03 DSM 23879, a strain of bacteria *Lactobacillus salivarius* LS06 DSM 26037 and a strain of bacteria *Lactobacillus fermentum* LF11 DSM 19188 in a weight ratio of 3:2:1, 3:1:1, 2:1:1, 2:2:1, or 1:1:1.

6. The method according to claim 1, wherein said composition further comprises a strain of bacteria *Streptococcus thermophilus* ST10 DSM 25246 and a tara gum.

7. The method according to claim 1, wherein said composition further comprises a gum.

8. The method according to claim 1, wherein said composition further comprises an *Aloe* gel, or a derivative thereof.

9. The method according to claim 1, wherein said composition further comprises *Bifidobacterium lactic* Bb 1 with deposit number DSM 17850, deposited at DSMZ on 23 Dec. 2005, by BioMan S.r.l. Company.

10. The method according to claim 1, wherein said composition is administered in an effective amount to protect gastric, esophageal and intestinal mucosae in the individual.

11. The method according to claim 3, wherein the bacterial concentration is from $1\times10^9$ UFC/g to $1\times10^{11}$ UFC/g.

12. The method according to claim 4, wherein the strain of bacteria *Lactobacillus reuteri* LRE03 DSM 23879 and the strain of bacteria *Lactobacillus salivarius* LS06 DSM 26037 are in a weight ratio from 1:3 to 3:1.

13. The method according to claim 4, wherein the strain of bacteria *Lactobacillus reuteri* LRE03 DSM 23879 and the strain of bacteria *Lactobacillus salivarius* LS06 DSM 26037 are in a weight ratio from 1:2 to 2:1.

14. The method according to claim 4, wherein the strain of bacteria *Lactobacillus reuteri* LRE03 DSM 23879 and the strain of bacteria *Lactobacillus salivarius* LS06 DSM 26037 are in a weight ratio of 1:1.

15. The method according to claim 4, wherein the strain of bacteria *Lactobacillus reuteri* LRE03 DSM 23879 and a strain of bacteria *Lactobacillus fermentum* LF11 DSM 19188 are in a weight ratio from 1:3 to 3:1.

16. The method according to claim 4, wherein the strain of bacteria *Lactobacillus reuteri* LRE03 DSM 23879 and a strain of bacteria *Lactobacillus fermentum* LF11 DSM 19188 are in a weight ratio from 1:2 to 2:1.

17. The method according to claim 4, wherein the strain of bacteria *Lactobacillus reuteri* LRE03 DSM 23879 and a strain of bacteria *Lactobacillus fermentum* LF11 DSM 19188 are in a weight ratio of 1:1.

18. The method according to claim 7, wherein said gum is an alginate, an alginate derivative, or a sodium alginate.

19. The method according to claim 8, wherein the *Aloe* gel is an *Aloe arborescens* gel.

20. The method according to claim 19, wherein the *Aloe arborescens* gel is freeze-dried.

\* \* \* \* \*